(12) United States Patent
Xie et al.

(10) Patent No.: US 12,133,701 B2
(45) Date of Patent: Nov. 5, 2024

(54) SAFE, EARLY WARNING METHOD AND SYSTEM FOR GUIDE WIRE MOVEMENT OF INTERVENTIONAL SURGICAL ROBOT

(71) Applicant: BEIJING WEMED MEDICAL EQUIPMENT CO., LTD, Beijing (CN)

(72) Inventors: Jing Xie, Beijing (CN); Tao Huang, Beijing (CN)

( * ) Notice: Subject to any disclaimer, the term of this patent is extended or adjusted under 35 U.S.C. 154(b) by 805 days.

(21) Appl. No.: 17/229,786

(22) Filed: Apr. 13, 2021

(65) Prior Publication Data

US 2022/0096182 A1 Mar. 31, 2022

Related U.S. Application Data

(63) Continuation of application No. PCT/CN2021/073730, filed on Jan. 26, 2021.

(30) Foreign Application Priority Data

Aug. 5, 2020 (CN) .......................... 202010779282.5

(51) Int. Cl.
*A61B 34/32* (2016.01)
*A61B 34/20* (2016.01)
*A61B 34/30* (2016.01)

(52) U.S. Cl.
CPC ............. *A61B 34/32* (2016.02); *A61B 34/20* (2016.02); *A61B 2034/2051* (2016.02); *A61B 2034/302* (2016.02)

(58) Field of Classification Search
CPC ............ A61B 34/20; A61B 6/00; A61B 34/32
See application file for complete search history.

(56) References Cited

U.S. PATENT DOCUMENTS

| 2008/0317195 | A1* | 12/2008 | Kobayashi | ............. | A61B 6/481 378/4 |
| 2014/0276233 | A1* | 9/2014 | Murphy | .................. | G01L 5/107 600/587 |
| 2015/0054929 | A1* | 2/2015 | Ito | .......................... | A61B 5/066 348/65 |
| 2016/0051794 | A1* | 2/2016 | Bian | .................. | A61M 25/0105 604/95.01 |

FOREIGN PATENT DOCUMENTS

CN 110882060 A * 3/2020

* cited by examiner

*Primary Examiner* — Angela M Hoffa
*Assistant Examiner* — Younhee Choi

(57) ABSTRACT

The method includes obtaining a distance value of a guide wire from an inner wall of cavity and a resistance value of the inner wall of cavity to the guide wire when the guide wire moves in the cavity and controlling the guide wire for corresponding movement according to a relationship between the distance value and a predetermined distance threshold value, and/or the relationship between the predetermined resistance threshold value. The alarm strategy through image and resistance detection multi-dimensionally, lead to low false alarm rate. Automatic error correction by automatic reverse motion avoids the risk of untimely correction in case of danger due to the user's stress during the movement, thus improving the overall automation of movement control of the intervention robot.

1 Claim, 4 Drawing Sheets

SAFE, EARLY WARNING METHOD AND SYSTEM FOR GUIDE WIRE MOVEMENT OF INTERVENTIONAL SURGICAL ROBOT

TECHNICAL FIELD

This disclosure relates generally to minimally invasive interventional surgery, and specifically, to a detection technology for a guide wire movement of a robot in an interventional operation. More specifically, the disclosure relates to a safe early warning method and system for the guide wire movement of an interventional surgical robot.

BACKGROUND

Minimally invasive interventional therapy is a new subject which has been developed rapidly in recent years and diagnostic imaging has been combined in clinical treatment. Conventional types of interventional operation require the doctor stands beside the catheter bed and performs the corresponding movement of the guide wire in combination with the image positioning information obtained by the real-time X-ray radiation acquisition. The typical interventional operation time is 40 minutes to 1.5 hours. It is difficult for doctors to avoid continuous exposure to X-rays. Especially in China, a large number of interventional doctors are overworked, and the operation volume is several times higher than that of Europe and American doctors. Long-term massive radiation results in a reduction of white blood cell, immune low, hair loss and a large number of occupational diseases, an increased incidence of white cell, cancer and other diseases, posing serious threat to the health of intervention doctors.

In order to solve the problem of excessive X-ray radiation suffered by the medical staff during the interventional operation, the research of the interventional surgical robot has arisen in recent years, which realize the movements of the guide wire and the catheter by simulating the hand movements of a doctor. It is of great clinical value for doctors to operate remotely, without the need to complete it beside the catheter bed, thus avoiding the radiation problem.

On the other hand, as an invasive operation with high risks, safety would always come first, especially for remotely controlled guide wire surgery aids such as interventional robots. Since the operator does not operate at the patient's site, it is not possible to collect a full view of the surgical site in a timely and effective manner, the operation risk is more likely to occur. It is necessary to avoid the injury of the inner cavity (blood vessel, non-blood vessel) caused by the unexpected movement of the guide wire through intelligent technology.

Therefore, it is an important research direction for those skilled in the art that how to safely warn the movement of the guide wire in the inner channel of the human body so as to overcome the above problems.

SUMMARY

The disclosure provides the safe early warning method and system for the guide wire movement of the interventional surgical robot, aiming to solve the problem that the existing auxiliary equipment of remote control of the guide wire movement cannot make real-time and effective warning and judgment of the dangerous movements of the guide wire. It provides technical support for the automatic control of the interventional robot.

Therefore, the purpose of the disclosure is to provide the safe early warning method for the guide wire movement of the interventional surgical robot, which includes the following steps:

Step 1, obtaining a distance value of the guide wire from an inner wall of the cavity and a resistance value of the inner wall of the cavity to the guide wire when the guide wire moves in the cavity;

Step 2, the guide wire is controlled for corresponding movement according to a relationship between the distance value and a predetermined distance threshold value, and/or the relationship between the resistance value and a predetermined resistance threshold value.

Preferably, the first step specifically includes acquiring detection images of the guide wire in the cavity, and calculating and analyzing the detection images to obtain the distance value of the guide wire from the inner wall of the cavity.

The disclosure provides an early warning mechanism for the guide wire, by detecting the distance value of the guide wire from the inner wall of the cavity and the resistance value of the inner wall of the cavity to the guide wire when the guide wire moves in the cavity. It realizes the self-correction in the operation process of using the interventional surgical robot, which solves the potential safety hazard that the existing surgical robot cannot self-correcting.

Preferably, the first step specifically includes triggering a pressure sensor by converting a movement process of the guide wire movement into the movement process of a force-measuring connecting rod, the displacement value of a force-measuring connecting rod is converted into the resistance value by the pressure sensor. The process of detecting the pressure value by the force-measuring connecting rod and the pressure sensor is carried out outside the body, which does not cause additional burden to the guide wire movement during the interventional robot surgery, and the detection results are accurate and reliable.

Preferably, the second step specifically includes automatically terminating the movement of the guide wire when the distance value between an end of the guide wire and the inner wall of the cavity exceeds the predetermined distance threshold value and the resistance value exceeds the predetermined resistance threshold value.

Preferably, the second step specifically includes automatically controlling the guide wire to continue performing the current movement when the distance value between an end of the guide wire and the inner wall of the cavity exceeds the predetermined distance threshold value but the resistance value does not exceed the predetermined resistance threshold value.

Preferably, the second step specifically includes automatically terminating a movement of the guide wire when the resistance value reaches the predetermined resistance threshold value in an advancing of the guide wire, and performing voice prompt and automatically controlling a retreating of the guide wire until the resistance value is lower than the predetermined resistance threshold value.

Preferably, the second step specifically includes automatically terminating a retreating of the guide wire when the guide wire resistance value reaches the predetermined resistance threshold value; and performing the voice prompt and automatically controlling the advancing of the guide wire until the resistance value is lower than the predetermined resistance threshold value.

Preferably, the second step specifically includes automatically terminating a rotation of the guide wire in the process of a guide wire rotation when the resistance value of the guide wire reaches the predetermined resistance threshold value; and performing the voice prompt and automatically controlling reverse rotation of the guide wire until the resistance value are lower than the predetermined resistance threshold value.

The disclosure provides the safe early warning system for the guide wire movement of the interventional surgical robot. The system includes an image detection device, a resistance detection device and a guide wire resistance conversion device and an interventional robot control device.

The image detection device is configured to acquire the detection images of the guide wire in the cavity;

the guide wire resistance conversion device is configured to transfer the displacement value to the resistance detecting device during the movement of the guide wire, and convert the displacement to different resistance triggering actions for the resistance detecting device;

the resistance detection device is configured to detect different resistance triggering actions and output resistance detection signals;

the interventional robot control device is electrically connected to the image detection device and the resistance detection device, and the interventional robot control device is configured to receive the the detection images and the resistance detection signals, and calculate and analyze to obtain the distance value between the guide wire and the inner wall of the cavity and the resistance value of the guide wire from the inner wall of the cavity, a control signal is output for the guide wire to perform the corresponding movement according to the relationship between the distance and the predetermined distance threshold value and the predetermined resistance threshold value.

Preferably, an intervention robot propulsion mechanism configured to grip the guide wire; wherein, the resistance detection device and the guide wire resistance conversion device are provided on the intervention robot propulsion mechanism, and the intervention robot propulsion mechanism is configured to transmit the displacement value in the guide wire movement.

The intervention robot propulsion mechanism is also configured to control the movement of the guide wire according to the control signal for the guide wire to perform the corresponding movement; the movement comprises: stop, advancing, retreating and rotation.

Preferably, the disclosure also includes an integrated sound acquisition module, which provides real-time voice prompts when the resistance value of the guide wire reaches the predetermined resistance threshold value, greatly enhancing the safety of the operation.

The resistance detection device and the guide wire resistance conversion device of the safe early warning method for guide wire movement of interventional surgical robot of the present disclosure are directly integrated with the intervention robot propulsion mechanism, with a high degree of system integration, a simple and reliable detection process, and no influence on the action control process of the guide wire.

The safe early warning method and system for guide wire movement of interventional surgical robot of the disclosure has the following beneficial effects:

1. Multi-dimensional setting of alarm strategy through image and resistance detection, leading to low false alarm rate.

2. Automatic error correction by means of automatic reverse motion avoids the risk of untimely correction in case of danger due to the user's stress during the operation.

3. Active prompting of users through sound to avoid the risk of unconscious misuse by users.

4. Improves the overall automation of movement control of the intervention robot.

BRIEF DESCRIPTION OF THE DRAWINGS

In order to illustrate the embodiments of the present disclosure or the technical solution in the prior art more clearly, a brief description of the embodiments or the drawings to be used in the description will be given below. And it is obvious that, the drawings in the following description are merely embodiments of the present disclosure, and other drawings may also be obtained from the drawings provided without any creative effort by those skilled in the art.

In the drawings.

Figure 1:
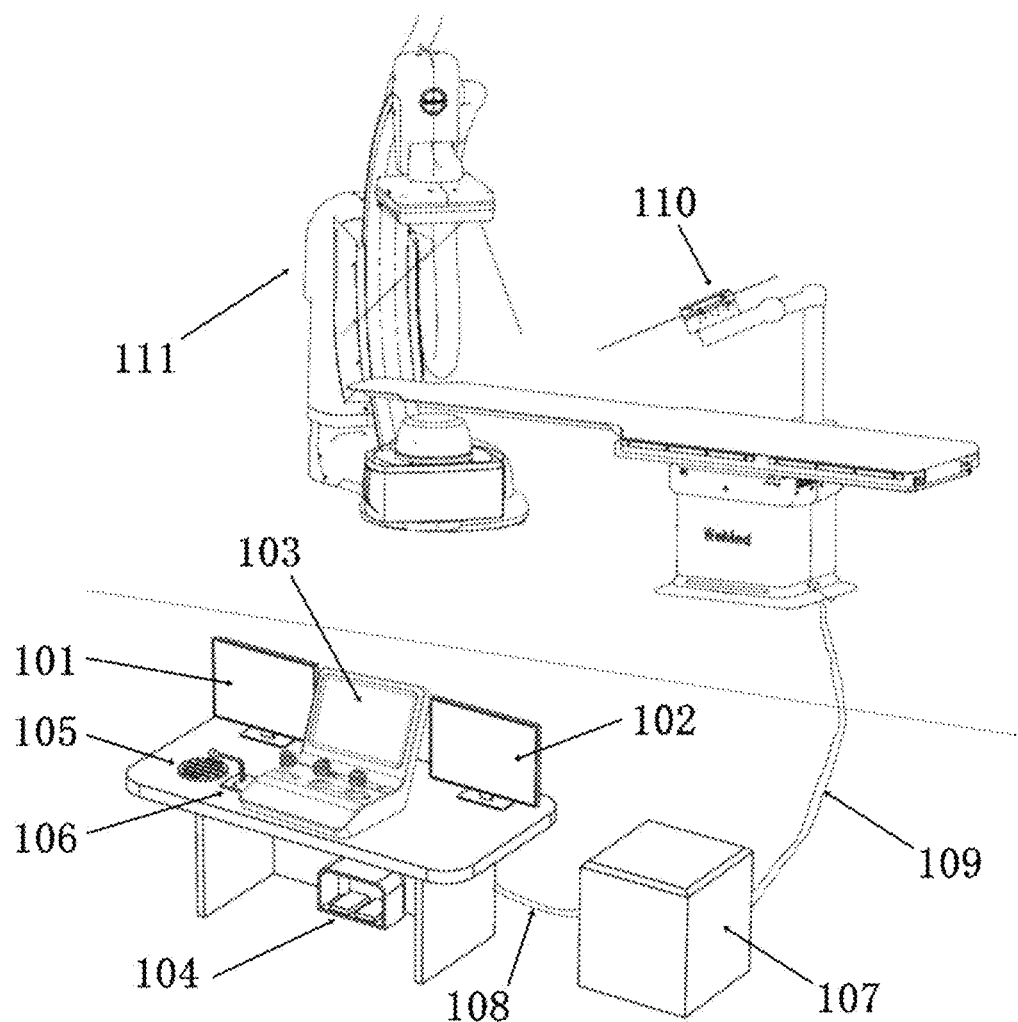
FIG. 1 is a structural schematic diagram of the safe early warning system for the guide wire movement for the interventional robot by the present disclosure.

101, 102—the digital subtraction angiography (DSA) image display, 103—the interventional robot control terminal, 104—the exposure control pedal, 105—loudspeaker, 106—microphone, 107—the interventional robot control device, 108—the connection cable of the controller of the interventional robot and the control device of the interventional robot, 109—the connection cable of the control unit of the interventional robot and the interventional robot, 110—the intervention robot propulsion mechanism, 111—the digital subtraction angiography (DSA) equipment, 201—the rocker of catheter motion, 202—the rocker of guide wire rotating, 203—the rocker of guide wire motion, 301—the guide wire, 302—the cam group, 303—the first fixed base plate, 304—the second fixed base plate, 305—the pressure sensor, 306—force-measuring connection member, 307—the electromagnet, 308—the first holding member, 309—the second holding member, 401—the communication module, 402—the video acquisition module, 403—the central processor unit, 404—the power module.

DETAILED DESCRIPTION OF EMBODIMENTS

Hereinafter, embodiments of the present disclosure will be described in detail, embodiments of which are shown in the accompanying drawings, in which the same or similar elements or elements having the similar or similar functions are denoted by the same reference numerals throughout. The embodiments described below by reference to the accompanying drawings are exemplary and intended to explain the disclosure and should not be construed as limiting the disclosure.

In the description of the disclosure, it is to be understood that, the terms "up", "down", "front", "back", "left", "right", "vertical", "horizontal", "top", "bottom", "inside", "outside" etc., the orientation or positional relationship indicated is based on the shown in the drawings, merely to facilitate the description of the disclosure and to simplify the description, rather than indicating or implying that the devices or elements referred to must have a particular orientation, be constructed and operate in a specific orientation, and therefore it should not be construed as limiting the disclosure.

In addition, the term "first," "second" are used for descriptive purpose only and are not to be construed as indicating or implying relative importance or implicitly indicate the number of technical features indicated. Thus, a feature defined as "first" or "second" may include one or more of the features, either explicitly or implicitly. In the description of the present disclosure, "plural" means two or more than two, unless otherwise specifically defined.

In the present disclosure, unless otherwise expressly specified and defined, the terms "install," "connect," and "fix" are to be understood in a broad sense. For example, a fixed connection or a detachable connection, or in one piece; either mechanically or electrically connected; either directly or indirectly connected through an intermediate medium, either in communication between the two elements or in an interactive relationship between them. The specific meanings of the above terms in the present disclosure may be understood by those of ordinary skill in the art as the case may be.

In the present disclosure, unless otherwise expressly specified and defined, the first feature is "up" or "down" to the second feature may comprise the first and second features in direct contact; it is also possible to include the first and second features not in direct contact but by means of a further feature contact between them. In addition, that word "up", "above" and "on" of the first feature include the first feature being directly above and obliquely above the second feature, or simply indicate that the level of the first feature is higher than that of the second feature. If the first feature is "down", "below" and "under" the second feature includes the first feature being directly below and diagonally below the second feature, or simply indicating that the height of the first feature is less than the second feature.

Embodiment

Referring to FIGS. 1-5, the safe early warning method and system for the guide wire movement of the interventional surgical robot of an embodiment of the present disclosure are described in detail.

Figure 4:
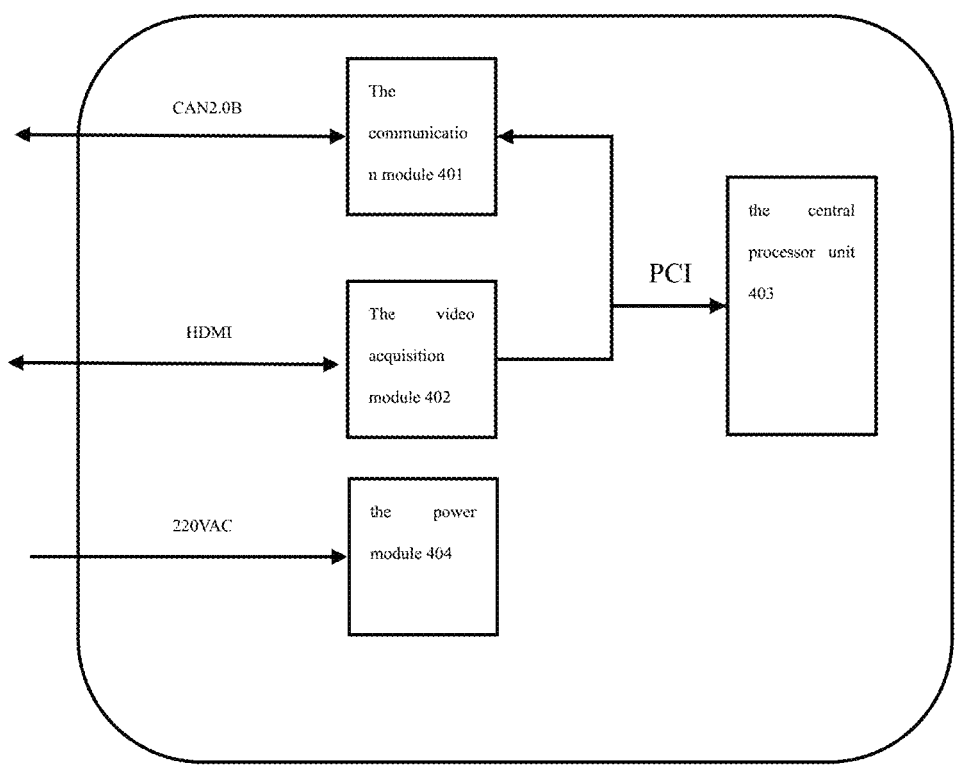
FIG. 4 is a composition block diagram of the interventional robot control device by the present disclosure.

Referring to FIGS. 1 and 4, a safe early warning system for the guide wire movement of the interventional surgical robot is disclosed. The system includes an image detection device, the resistance detection device, the guide wire resistance conversion device, the interventional robot control terminal 103, the exposure control pedal 104, the interventional robot control device 107, the connection cable of the controller of the interventional robot 108 and the control unit of the interventional robot, the connection cable of the control unit of the interventional robot and the interventional robot 109, an intervention robot propulsion mechanism 110.

The image detection device is used to obtain the detection images of the guide wire in the cavity. A DSA equipment 111 can be used, and the DSA equipment 111 contains a video acquisition card 402 for collecting angiography images.

The guide wire resistance conversion device transmits the displacement value during the guide wire moves to the resistance detection device and converts it into a different resistance trigger actions for the resistance detection device.

The resistance detection device detects the different resistance triggering actions and outputs a resistance detection signal, which is transmitted to the central processor unit 403 of the interventional robot control device 107 through the communication module 401.

The interventional robot control device 107 is electrically connected to the image detection device and the resistance detection device for receiving the detection images and the resistance detection signals. The central processor unit 403 calculates and analyzes the distance value of the guide wire from the inner wall of the cavity and the resistance value of the cavity wall to the guide wire, and outputs a control signal for the guide wire to perform the corresponding movement according to the relationship between the distance value and the predetermined distance threshold value, and/or the resistance value and the predetermined resistance threshold value. The interventional robot control device 107 also has the power module 404 to provide electrical power supply to the central processor unit 403 and the corresponding components.

The intervention robot propulsion mechanism 110 receives the control signals generated by the interventional robot control device 107 to realize the automatic control process and receives the control signals sent by the intervention robot control terminal 103 to realize the manual control process.

The interventional robot control device 107 is connected to two DSA image monitors 101, 102 for displaying the test images collected by the DSA equipment 111.

The interventional robot control device 107 is also connected to the loudspeaker 105, microphone 106 for voice prompt function and voice capture function.

Figure 2:
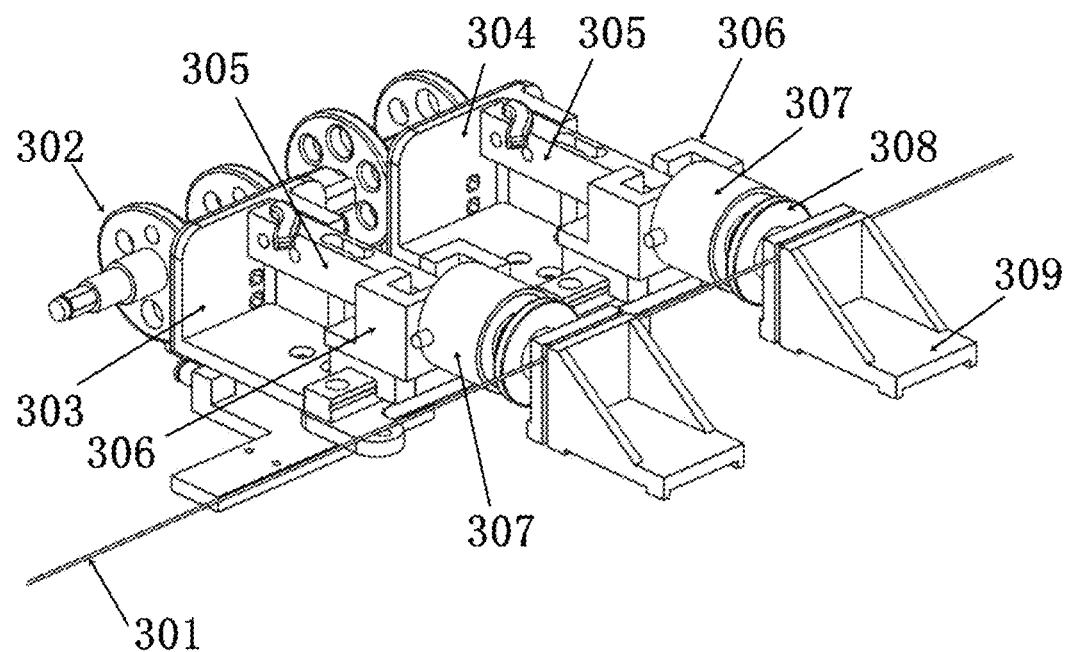
FIG. 2 is an installation structure diagram of the resistance detecting device and the guide wire resistance conversion device by the present disclosure.

Referring to FIG. 2, the guide wire 301 is clamped on two sets of the first holding member 308 and the second holding member 309. The first holding member 308 is slidable along the length of the guide wire 301 under the control of the motor to provide power for the two sets of holding members of the interventional surgical robot to alternately push and pull the guide wire. The second holding member 309 moves perpendicular to the length of the guide wire 301 under the control of the motor to provide power for the two sets of holding members of the interventional surgical robot to clamp the guide wire. The first holding member 308 and the second holding member 309 can slide up and down in the direction parallel to the clamping surface of the first holding member 308 under the control of the motor to provide the power for the two holding members of the interventional surgical robot to rotate the guide wire. The guide wire resistance conversion device is installed on one side of the first holding member 308. The guide wire resistance conversion device includes a disassembly structure and a force measuring connection member 306 connected to the disassembly structure, in which the disassembly structure can be an electromagnet 307, and the electromagnet 307 absorbs and fixes the second holding member 309 and the force measuring connection member 306 as a whole. Two pressure sensors 305 are respectfully fixed by the first fixed base plate 303 and the second fixed base plate 304. The first fixed base plate 303 and the second fixed base plate 304 can be moved in the lengthwise direction of the guide wire 301 under the motor driving control, for driving the pressure sensor 305, the force-measuring connector 306, the disassembling structure, the first holding member 308 and the second holding member 309 to reciprocate, so as to advance and retreat the guide wire in the human body cavity by alternately reciprocating pulling and pulling the guide wire. After the guide wire 301 is clamped, the force measuring connection member 306, disassembly structure, the first holding member 308 and the second holding member 309 are slidingly connected to the first fixed base plate 303/the second fixed base plate 304 as a moving unit, and the connection method includes the force measuring connection member 306 mounted on the first fixed base plate 303/the second fixed base plate 304 through the slider and guide rail; the second holding member 309 can be connected to the first fixed base plate 303/the second fixed base plate 304 by the same sliding connection method in order to maintain the synchronous displacement with the force measuring connection member. The above structure is used to provide micro-displacement relative to the pressure sensor 305 when the guide wire 301 is subjected to resistance.

The force measuring connection member 306 has two convex edges set opposite to each other, the direction of the convex edges is the length direction of the guide wire 301. The sensing end of the pressure sensor 305 is located between the two convex edges and is in contact with the two convex edges, when there is a force change on the guide wire 301, the small deformation will be transferred to the pressure sensor 305 through the force measuring connection member 306, so as to measure the force change.

Two cam groups 302 are located at the rear of the first fixed base plate 303 and the second fixed base plate 304, which are controlled by stepping motor to rotate around the same axis to push the first fixed base plate 303 and the second fixed base plate 304 to move alternately in the direction perpendicular to the guide wire 301, thus driving the alternate movement of the first holding member 308 to achieve the purpose of automatic alternate clamping and loosening of the guide wire.

Figure 3:
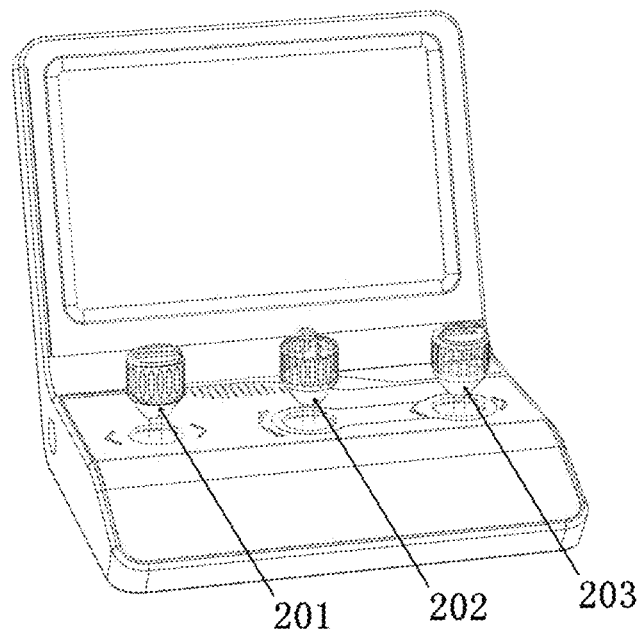
FIG. 3 is a structure diagram of the interventional robot control terminal by the present disclosure.

Referring to FIG. 3, the interventional robot control terminal 103 is equipped with the rocker of catheter motion 201, the rocker of guide wire rotation 202, and the rocker of guide wire motion 203 for manually manipulating the output control signals to the intervention robot propulsion mechanism 110.

Figure 5:
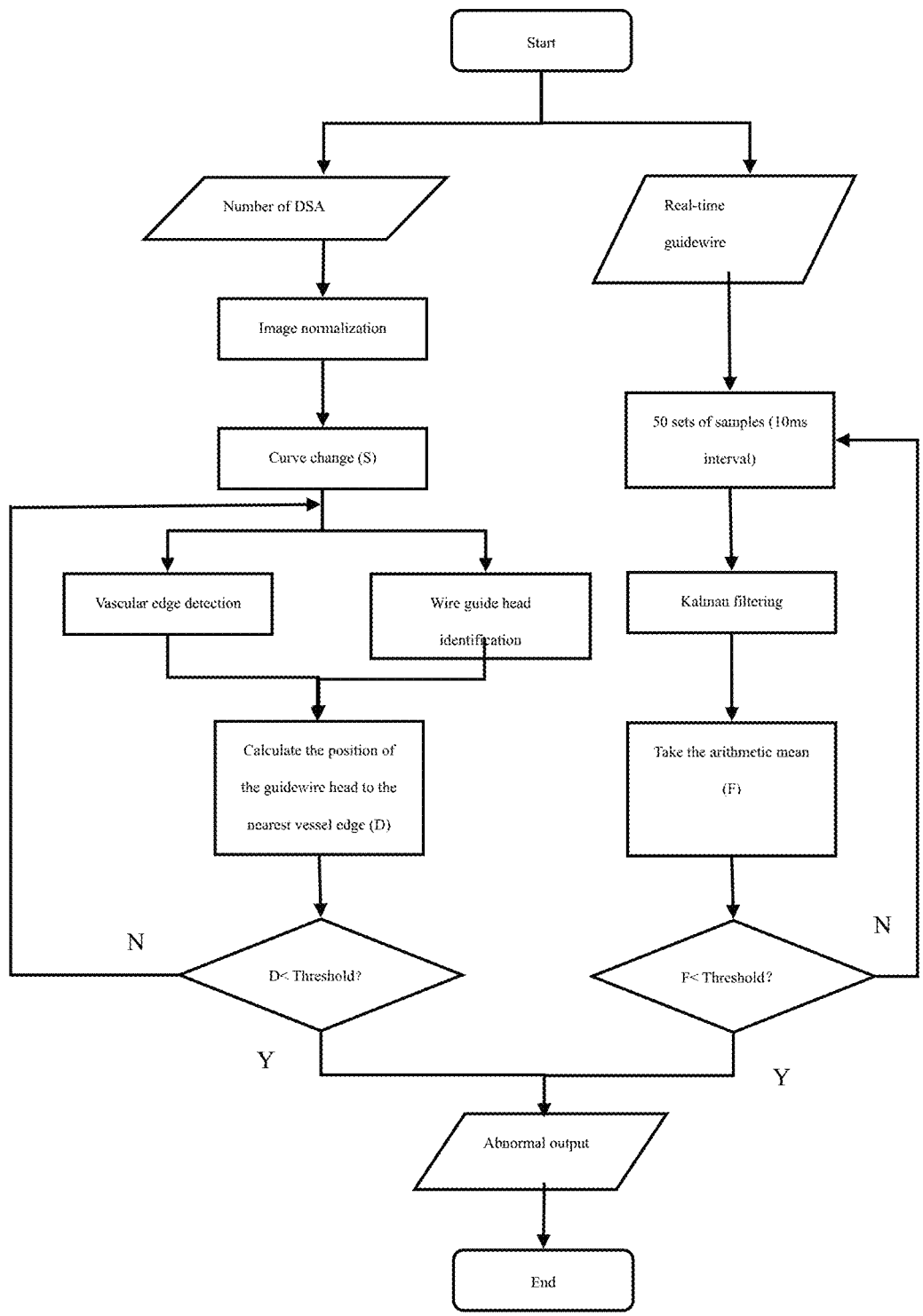
FIG. 5 is a flow chart of the safe early warning method for the guide wire movement for the interventional robot by the present disclosure.

Referring to FIG. 5, another embodiments of the safe early warning method for the guide wire movement of the interventional surgical robot is disclosed.

Step 1, obtaining a distance value of a guide wire from the inner wall of the cavity and the resistance value of the inner wall of the cavity to the guide wire when the guide wire moves in the cavity.

Step 2, controlling the guide wire to perform the corresponding movement according to the relationship between the distance value and the predetermined distance threshold value, and/or the relationship between the resistance value and the predetermined resistance threshold value.

The specific execution of obtaining the distance and resistance value in step 1 includes:

Obtaining the detection images of the guide wire in the cavity, then calculating and analyzing the distance value of the guide wire from the inner of the cavity based on the detection images.

Triggering the pressure sensor by converting the movement process of the guide wire movements into the movement process of the force-measuring connecting rod, the displacement value of the force-measuring connecting rod are converted into the resistance value by the pressure sensor.

The specific execution process to control the corresponding action of the guide wire in step 2 includes When the distance of the end of the guide wire from the inner wall of the cavity exceeds the predetermined distance threshold value and the resistance value exceeds the predetermined resistance threshold value, the automatic control of the guide wire stops the movement.

When the distance between the end of the guide wire and the inner wall of the cavity exceeds the predetermined distance threshold value but the resistance value does not exceed the predetermined resistance threshold value, the automatic control of the guide wire continues to perform the current movement.

In the process of advancing the guide wire, if the resistance value of the guide wire reaches the predetermined resistance threshold value, the automatic control of the guide wire stops the advancing movement, makes a voice prompt and automatically controls the guide wire to perform the backward movement until the resistance value is lower than the predetermined resistance threshold value.

In the process of guide wire backward, if the guide wire resistance value reaches the predetermined resistance threshold value, automatically control the guide wire to stop the backward action, voice prompts and automatically control the guide wire to perform forward movement until the resistance value is lower than the predetermined resistance threshold value.

In the process of guide wire rotation, if the guide wire resistance value reaches the predetermined resistance threshold value, automatic control in the guide wire to stop the rotation movement, voice prompts and automatic control in the guide wire to perform the reverse direction of rotation movement until the resistance value is lower than the predetermined resistance threshold value.

A working principle of the system is:

When the first holding member 308 clamps the guide wire 301, the guide wire is driven by the cam group 302 for movement. When the guide wire 301 is subjected to resistance during travel, the friction between the surface of the guide wire and the first holding member 308 and the second holding member 309 changes, and the resistance value of the guide wire is collected by the pressure sensor 305. The resistance value is transmitted to the control unit of the interventional robot 107 through the can protocol via the cable 109 by the intervention robot propulsion mechanism 110.

The inspection images acquired by the DSA equipment 111 are transmitted to the interventional robot control device 107 as an HDMI video stream through the DSA universal HDMI interface via cable 109.

After the central processing unit 403 collects the current resistance value, it is stored in real time, smoothed and de-jittered by Kalman filtering, and compared with the preset resistance threshold value. If it is larger than that the resistance threshold value, it is considered that it is in a high-risk state, and relevant instruction are sent to the intervention robot propulsion mechanism 110 through the cable 109. The intervention robot propulsion mechanism 110 stops the movement of the guide wire by controlling the internal cam group and other corresponding mechanisms.

The central processor unit 403 firstly preprocesses the original images by normalization and curve stretching once after the current DSA angiography images are collected, And then the central processor unit 403 identifies the position of the guide wire head and the contour of the vessel wall edge based on the morphological detection method, calculates the distance value of the guide wire from the vessel wall edge, and compares the distance value with the distance threshold value. If it is less than the predetermined resistance threshold value, it is considered to be in a high risk state. The relevant instruction is sent to the intervention robot propulsion mechanism 110 through the cable 109, and the propulsion mechanism 110 stops the relevant movement of the guide wire by controlling the internal cams and other corresponding mechanisms.

Under normal circumstances, the three main movements of the guide wire (advance, retreat and rotation) are controlled by a combination of three rockers on the intervening robot controller 103, and the following is an introduction to the actual control process.

When using the rocker of catheter motion 203, the interventional robot control device 107 sends the control command to the intervention robot propulsion mechanism 110, and intervention robot propulsion mechanism 110 moves forward and backward according to the motion command, while the interventional robot control device 107 simultaneously analyzes the guide wire resistance value transmitted by the intervention robot propulsion mechanism 110 and the DSA images transmitted by the DSA equipment 111, and once it determines the danger, it sends the command. Once the danger is judged to have occurred, a command will be sent to the a intervention robot propulsion mechanism 110 to control its automatic movement in the opposite direction of the current movement, and a loudspeaker 105 will be used to alarm the robot until the interventional robot control device 107 analyzes that the current risk has been removed based on the guide wire resistance value transmitted by the intervention robot propulsion mechanism 110 and the DSA images transmitted by the DSA equipment 111, and a stop command will be sent to the advancement mechanism of the interventional robot 110 to stop the current movement and stop the loudspeaker 105 alarm.

When using the rocker of guide wire rotation 202, the interventional robot control device 107 sends control commands to the intervention robot propulsion mechanism 110, and the intervention robot propulsion mechanism 110 realizes clockwise and counterclockwise rotation of the guide wire according to the motion command. The interventional robot control device 107 synchronously carries out DSA images analysis according to the guide wire resistance value transmitted by the intervention robot propulsion mechanism 110 and the DSA equipment 111. Once the danger is judged to have occurred, a command will be sent to the intervention robot propulsion mechanism 110 to control its automatic movement in the opposite direction of the current movement, and a loudspeaker 105 alarm will be automatically generated until the interventional robot control device 107 analyzes that the current risk has been removed based on the guide wire resistance value transmitted by the advancement mechanism of the interventional robot and the DSA images transmitted by the DSA equipment 111, a stop command will be sent to the intervention robot propulsion mechanism 110 to stop the current movement and stop the loudspeaker 105 alarm.

When using the rocker of guide wire motion 201, the interventional robot control device 107 sends control commands to the intervention robot propulsion mechanism 110, and the intervention robot propulsion mechanism 110 and retreats the catheter according to the motion commands, while the interventional robot control device 107 simultaneously analyzes the DSA images transmitted by the interventional robot and the DSA equipment 111 according to the guide wire resistance value transmitted by the interventional robot 110. Once the danger is judged to have occurred, the robot control device will send a command to the intervention robot propulsion mechanism 110 to control its automatic movement in the opposite direction of the current movement, and automatically alarm through the loudspeaker 105 until the interventional robot control device 107 analyzes that the current risk has been removed based on the guide wire resistance value transmitted by the intervention robot propulsion mechanism 110 and the DSA images transmitted by the DSA equipment 111, and will send a stop command to the intervention robot propulsion mechanism 110 to stop the current movement and stop the loudspeaker 105 alarm.

Each embodiment in this specification is described in a progressive manner, with each embodiment focusing on the differences from the other embodiments, and the same and similar parts between each embodiment can be referred to each other. For the device disclosed in the embodiment, because it corresponds to the method disclosed in the embodiment, so the description is relatively simple, and the relevant parts can be described in the method section.

The foregoing description of the disclosed embodiments enables those of skill in the art to implement or use the present disclosure. A plurality of modifications to these embodiments will be apparent to those skilled in the art, and the general principles defined herein can be implemented in other embodiments without departing from the spirit or scope of the present disclosure. Thus, the disclosure will not be limited to these embodiments shown herein, but will be subject to the widest scope consistent with the principles and novel features disclosed herein.

What is claimed is:

1. A safe, early warning system for guide wire operation of interventional surgical robot, comprising:
    an image detector a first fixed base plate coupled to a first pressure sensor, a second fixed base plate coupled to a second pressure sensor, a first guide wire resistance converting device coupled to a first holding member and the first pressure sensor, a second holding member coupled to the first holding member, a second guide wire resistance converting device coupled to the second pressure sensor and a third holding member, a fourth holding member coupled to the third holding member, and an interventional robot controller;
    wherein the image detector is configured to acquire detection images of a guide wire in a cavity;
    the first and second guide wire resistance converting devices each comprise an electromagnet and a force measuring connection member connected to the electromagnet; the first and second guide wire resistance converting devices are each configured to transfer a displacement value to the respective first pressure sensor and the second pressure sensor during a movement of the guide wire,
    the first pressure sensor and the second pressure sensor are configured to detect the displacement value and output resistance detection signals;
    the interventional robot controller is electrically connected to the image detector, and the interventional robot controller is configured to receive the detection images and the resistance detection signals, and calculate and analyze to obtain a distance value between the guide wire and an innerwall of the cavity and a resistance value of the guide wire from the inner wall of the cavity;
    a control signal is output for the guide wire to perform a corresponding movement according to a relationship between the distance value and a predetermined distance threshold value, and a relationship between the resistance value and a predetermined resistance threshold value;
    wherein the guide wire is configured to be clamped between the first holding member and the second holding member and between the third holding member and the fourth holding member; each of the first holding member and third holding member is slidable along a length of the guide wire; each of the second holding member and fourth holding member moves perpendicular to the length of the guidewire; each of the first holding member, the second holding member, the third holding member, and the fourth holding member slide up and down in the direction parallel to a clamping surface of each of the first holding member and third holding member;

the first fixed base plate and the second fixed base plate move in a lengthwise direction of the guide wire for alternately driving the two pressure sensors to advance and retreat the guide wire.

\* \* \* \* \*